United States Patent [19]
Kaefer-Hoffmann et al.

[11] Patent Number: 6,005,388
[45] Date of Patent: Dec. 21, 1999

[54] DEVICE AND PROCESS FOR DETECTING DEFECTS IN THE DISPOSITION OF REINFORCING MEMBERS OF MAGNETIZABLE MATERIAL IN CASING PLIES IN THE SIDEWALL REGION OF A TIRE

[75] Inventors: Michaela Kaefer-Hoffmann, Wedemark; Werner Bosch, Garbsen, both of Germany

[73] Assignee: Continental Aktiengesellschaft, Hannover, Germany

[21] Appl. No.: 08/862,614

[22] Filed: May 23, 1997

[30] Foreign Application Priority Data

May 25, 1996 [DE] Germany ............................ 196 21 198

[51] Int. Cl.⁶ ..................... G01N 27/82; G01M 17/02; B60C 11/24
[52] U.S. Cl. ........................... 324/240; 73/146; 209/538; 209/567; 324/226; 324/242; 324/261; 324/262
[58] Field of Search ........................... 324/226, 227, 324/228, 237, 238, 240–242, 261, 262; 73/146; 209/538, 567, 571; 702/38, 199

[56] References Cited

U.S. PATENT DOCUMENTS

| | | |
|---|---|---|
| 3,698,971 | 10/1972 | Matthews . |
| 3,974,399 | 8/1976 | Oyama et al. . |
| 4,004,693 | 1/1977 | Tsuji et al. . |
| 4,311,044 | 1/1982 | Marshall et al. ............... 73/146 |
| 5,060,173 | 10/1991 | Tsuji ............................ 73/146 X |
| 5,165,273 | 11/1992 | Church ........................ 73/146 |
| 5,216,372 | 6/1993 | Zoughi et al. . |
| 5,313,827 | 5/1994 | Yovichin . |
| 5,410,439 | 4/1995 | Egbert et al. ................. 324/212 X |
| 5,559,437 | 9/1996 | Baccaud et al. . |

FOREIGN PATENT DOCUMENTS

| | | |
|---|---|---|
| 0590436 | 4/1994 | European Pat. Off. . |
| 0681181 | 11/1995 | European Pat. Off. . |
| 2433178 | 3/1980 | France . |
| 2520435 | 11/1975 | Germany . |
| 3301173 | 7/1984 | Germany . |
| 3546149 | 10/1989 | Germany . |
| 4223248 | 1/1994 | Germany . |

*Primary Examiner*—Gerard Strecker
*Attorney, Agent, or Firm*—Greenblum & Bernstein, P.L.C.

[57] ABSTRACT

Device and process for detecting defects in an arrangement of reinforcing members in casing plies in a sidewall region of at least one of an unvulcanized tire blank or a vulcanized pneumatic vehicle tire to be tested. The reinforcing members may include a magnetizable material and the device may include a support device that rotatably supports the at least one of the unvulcanized tire blank or the vulcanized pneumatic vehicle tire in rotation around a rotational axis and at least one sensor that measures magnetic field intensities in a heterogeneous magnetic field resulting from inductions generated by the defects in the arrangement of the reinforcing members moving through the heterogeneous magnetic field. The at least one sensor may be positioned in a radial measuring position in a radial region of the sidewall. The device may also include a rotation controller that controls the rotation of the unvulcanized tire blank or the vulcanized pneumatic vehicle tire and an evaluation device coupled to the at least one sensor to receive the detected magnetic field intensities.

42 Claims, 4 Drawing Sheets

DEVICE AND PROCESS FOR DETECTING DEFECTS IN THE DISPOSITION OF REINFORCING MEMBERS OF MAGNETIZABLE MATERIAL IN CASING PLIES IN THE SIDEWALL REGION OF A TIRE

CROSS-REFERENCE OF RELATED APPLICATION

The present invention claims the priority under 35 U.S.C. §119 of German Patent Application No. 196 21 198.0 filed on May 25, 1996, the disclosure of which is expressly incorporated by reference herein in its entirety.

BACKGROUND OF THE INVENTION

1. Field of the Invention

The present invention relates to a device and a process for detecting defects in an arrangement (disposition) of reinforcing members. The reinforcing members may include magnetizable material, e.g., steel, in casing plies in the sidewall region of an unvulcanized tire blank or a vulcanized pneumatic vehicle tire.

2. Discussion of Background Information

Pneumatic vehicle tires are generally made with one or a plurality of casing plies having parallel reinforcing members imbedded inside. The casing plies usually extend from one bead core, over a sidewall, a crown region, another sidewall, and to a second bead core. While the crown region is usually additionally reinforced by belt plies, the sidewall gets its strength and resistance, i.e., relative to foreign bodies from outside and relative to internal pressure, mainly from reinforcing members within the casing. Accordingly, irregularities in the arrangement or positioning (spacing) of the reinforcing members of the casing can be particularly disadvantageous, especially in a vicinity of the sidewall. That is, irregularities, e.g., in the form of enlarged spaces between reinforcing members, lead to full-blown weak points of the sidewall. In the operating state of a vehicle, internal pressure of the tire can lead to excess strain of the rubber material and bulging and, in the long term, to the tearing of the rubber material. Because foreign bodies can penetrate this region with particular ease, tire blowouts may consequently result. Further, even smaller damages to the rubber material of the tire can easily lead to the tearing of the rubber material in the region of the weak point.

Since defects of the type described above, i.e., in the arrangement (spacing) of the reinforcing members, can still occur in a wide variety of ways during the construction of the tire and with the production of the torus form, it is important to utilize quality controls of the toroid pneumatic vehicle tire so as to achieve early detection of arrangement deviations of the reinforcing members in the sidewall region. These detected deviations exceed maximal permissible values based on experimental values. With retreads or used tires, it is also important to be able to detect these substantially impermissible irregularities early, e.g. after more intense contact of the sidewall with curb edges or other hard objects.

In the prior art, it is conventional for pneumatic vehicle tires having casings with reinforcing members of steel to be X-rayed after vulcanization. The tire is X-rayed all around the tire circumference. This permits the circumferential arrangement or position of impermissible arrangement deviations and the member sizes to be precisely determined by measuring the spacings. X-ray apparatuses of the type utilized in this environment generally require a large cost expenditure for installation and maintenance. Further, wear and tear on costly, sensitive X-ray tubes is considerably high. In order to protect the environment and the health of operating personnel, further high cost expenditures are necessary for additional devices, e.g., X-radiation shielding. Still further, when testing tires in series production, continuous optical evaluation of X-ray images, which exhibit a large number of parallel, closely adjacent, dark reinforcing members in the brightly lit surroundings, is fatiguing for operating personnel. Additional cost expenditures are necessary to protect against X-radiation and damage to the display unit due to fatigue when it is frequently actuated. The X-ray apparatus also requires a large number of additional subassemblies, e.g., for cooling, that are cost-intensive electronic equipment for control and evaluation of the overall X-ray apparatus. Further, the entire measuring station, with all of the corresponding protective measures and subassemblies and the large number of components, takes up a considerable amount of space.

Since a minimum measurement time is required for each tire measurement, an increase in the tire production beyond a particular measure signifies a requirement for installing additional cost-intensive X-ray apparatuses. These additional x-ray apparatuses, suffer from the disadvantages noted above, e.g. costly maintenance, protection, assembly, operation, and storage space. Due to the high cost, the x-ray apparatuses are generally only used at the end stage of tire production, in which all of the manufacture conditional arrangement or position deviations can be detected. Since positioning defects of the reinforcing members can also occur within the vulcanization apparatus and during vulcanization, X-ray apparatuses of the type discussed above are generally only used on the finished, vulcanized vehicle tire. However, tires having impermissible arrangement or position deviations, cannot be repaired when such defects are detected in this late, vulcanized state. Further, as scrap, these vulcanized finished tires can hardly be reused.

Due to the high expenditure necessary for maintaining and utilizing X-ray apparatuses, automobile shops and other maintenance personnel are generally unable to perform the above described checks during the service life of the tire. Even when the apparatuses are available, the checks are generally performed on a limited basis and at a significant cost.

German Patent document No. DE 42 23 248 A1 has disclosed the detection of defects in wide steel cord strips through the use of a magnetic field leakage process. For example, in the production of flat casing belts, the steel cord strips are drawn across a metal plate so that an angle of greater than 0° is produced between the direction of movement and the alignment of the steel cords. Detectors of the type, e.g., SND 6 by Roland Electronik GmbH, D-7538 Keltern 2, which had previously been used for monitoring welding seams, are located beneath the metal plate. In this process, the detectors produce a heterogeneous magnetic field. The steel cord strips are moved through, and in a direction of, the magnetic field, to influence the heterogeneous magnetic field as a function of the spacing of the steel cords relative to each another. The detectors determine a magnetic field intensity resulting from induction arising at the defects and immediately indicate the magnetic field intensity change. The cord strip is stopped and the defective place is immediately removed so that the casing material, which is produced in belt form, can be used in a perfect state for further production of the tire. In this manner, defects in the casing material that exist in the production of the casing belts can be detected and removed.

However, arrangement or positioning defects between the reinforcing members of the casing, which are produced from the different plies and layers, in the transport of the plies to construction, in the raising the plies and layers for producing the torus shape, in the bonding of the casing packet with the tread and belt, in the raising and lowering of assembly drums, and/or in other actions after the manufacture of the flat, smooth, belt-shaped, half-finished casing product cannot be detected with the process and device of DE 42 23 248 A1. In order to detect defects of this kind, in a practical conversion, the aforementioned X-ray process, with all of its associated disadvantages, must be relied upon.

SUMMARY OF THE INVENTION

An object of the present invention is to produce a device and a process for simple, reliable detection of defects in the arrangement and location of reinforcing members made of magnetizable material, e.g., steel, in the casing ply in a sidewall region of a toroid tire blank or a vulcanized pneumatic vehicle tire.

The object may be achieved according to the present invention by a device that includes a device for rotatably supporting the tire blank or pneumatic vehicle tire to be tested around its axis, and at least one sensor for detecting magnetic field intensity resulting from induction arising from defects in the arrangement of the reinforcing members moving past the at least one sensor. The at least one sensor may generate a heterogeneous magnetic field and may be located, at least during measuring, in a radial measurement position in the radial region of the sidewall. The device may also include a radial adjusting device for adjusting the radial measurement position of the sensor into a radial set position of the tire, in which the radial set position of the tire is a function of tire diameter. The device may also include an axial adjusting device for adjusting an axial distance between the at least one sensor and the sidewall to be measured, a controller for controlling rotation of the tire blank or pneumatic vehicle tire to be tested, and an evaluation device coupled to the at least one sensor for transmitting the measured, resulting field intensity of the magnetic field.

With the aid of a rotary support, a tire blank or pneumatic vehicle tire to be tested may be received for testing so that it can rotate around its axis in the device. The controlled rotation device changes a rotational position of the tire in the device so that the reinforcing members of the sidewall, which are aligned to enclose an angle greater than 0° relative to a circumference direction, may be moved past the sensor in the sidewall region. The sensor detects a magnetic field intensity resulting from induction generated in a heterogeneous generated magnetic field by defects in the arrangement or positioning of the reinforcing members moving relative to the heterogeneous magnetic field. The sensor, at least during measurement, may be located in stationary fashion in a radial measurement position in a radial region of the sidewall and may enclose an angle between the reinforcing members and the movement direction and an angle between the reinforcing members and the magnetic field direction. Consequently, the heterogeneous magnetic field may be influenced by inductions generated by defects in the arrangement or positioning of the reinforcing members that change the resulting magnetic field intensity. The changes in magnetic field intensity produced by the defects may be measured by the sensors and transmitted to an evaluation device. With the evaluation device, it may also be possible to detect the position of defects in the arrangement or positioning of reinforcing members in a tire blank embodied in the form of a torus or in a completed, vulcanized pneumatic vehicle tire with the aid of the simple magnetic field leakage process.

An apparatus of the above-described type may be simple and reasonably priced and the expenditure for protecting health and the environment from X-radiation may be eliminated. The magnetic sensors experience very little wear and tear and expenditures for the X-ray tube, diode counting system for image generation of X-ray images, and independent cooling are eliminated. The fatiguing due to optical effort, e.g., for monitoring X-ray images, may also be eliminated. Further, a device of this kind is structurally simple and can be embodied in a space-saving manner. The low cost expenditure for production and maintenance, and the lack of devices for protection against X-radiation permit economical use even before vulcanization of the tire, so that the defects produced during formation of the torus and before vulcanization can be detected. The tire blanks, which have been determined at this early stage to have defects, can simply be reworked or separated and reused. Moreover, the device of the present invention permits testing of already completed, vulcanized pneumatic vehicle tires in which the defects, which are produced during the remaining raising in the vulcanization vat and in the vulcanization, may also be detected. In particular, with an adjustment device for adjusting the radial position of the sensor as a function of tire diameter into a radial set position of the tire, an ideal measurement position in the sidewall region may be adjusted for each tire dimension so that extremely varied tire dimensions may be tested in a simple and individual manner as needed. The optimization of measurement quality is made possible by adjusting the axial distance between the sensor and the sidewall to be measured. Particularly, the optimal spacing between the sensor and the sidewall may be individually adjusted for each tire width. The low cost permits flexible change of the location at which the device is utilized and a simple, reasonably priced testing of vehicle tires during their entire service life, e.g., in automobile or tire repair shops.

Further, the object of the present invention may be achieved by a process that includes moving reinforcing members relative to a sensor, the reinforcing members arranged to form an angle greater than 0° between a direction of movement and an alignment of the reinforcing members, and measuring magnetic field intensities in a heterogenous magnetic field produced by induction due to the relative movement. Rotating the tire blank or pneumatic vehicle tire in a first angular range, and determining an average value of the measured magnetic field intensities. Rotating the tire blank or pneumatic vehicle tire in a second angular range, and measuring the magnetic field intensity in the second angular range. The process may also include determining deviations of the measured values of the second angular range relative to the average value of the first angular range. The deviations may be compared to set values for the permissible deviations, and indicating a rotational angle or circumferential position of defects having deviations greater than the set value adjacent corresponding reinforcing members of the tire sidewall.

Without a great deal of operational expenditure, in a first step of the process of the present invention, the tire blank or the pneumatic vehicle tire may be rotated in a first angular range, and a course or plot of the magnetic field intensity, i.e., resulting from induction during the motion due to the arrangement or positioning of the individual reinforcing members in the angular range in the heterogeneous magnetic field, may be measured and an average value may be determined over the angular range. Subsequently, the rotation of the tire may be continued through a further angular range, and the course of the resulting magnetic field intensity produced over this angle of rotation may be determined. This subsequent course of the magnetic field intensity may be compared to the average value, i.e., which was determined in the first step of the process and is utilized as a reference value, and may be utilized to indicate deviations from the average value determined. The deviations may be compared over an entire angular range, i.e. over the circumference region of the test piece, with predetermined set values for the maximum permissible deviations from the average value. The circumference position of the deviations, i.e., which fall outside a desired value, represent the circumference positions on the test piece at which adjacent reinforcing members have positional deviations above the maximal permissible tolerance values corresponding to the set value. These positions may be indicated as an angle of rotation or as a circumferential position of arrangement or positional defects of adjacent reinforcing members in the tire sidewall. In this manner, the position of defects in the arrangement of the reinforcing members can be determined in a simple and reliable manner for each tire, e.g., by averaging the measured magnetic field in the tire and then subsequent individual determination of the deviation from the average value by comparison with the set value, e.g., a measure for permissible tolerance. The set value can be predetermined in accordance with the requirements for the tire to be tested, its construction, and the resulting maximal permissible values for deviations from an optimal value for the spacing between adjacent reinforcing members. By utilizing the process of the present invention, the high cost required to carry out the determinations using X-rays is substantially eliminated.

The process in accordance with an embodiment of the present invention, permits individual determination of the size of the arrangement or position defects, in which the X-ray process is no longer required for each pneumatic vehicle tire or blank, but only in those pneumatic vehicle tires or tire blanks in which the existence and position of these defects has actually been determined by the magnetic field leakage process of the present invention. As a result of this, the application and the dangers to human health and the environment are reduced to a minimum of transitory stress. By including an X-ray device, a high production number of tires can consequently also be reliably tested in a qualitatively permissible fashion as to the position and size of arrangement or positional defects of reinforcing members in tire sidewalls while minimizing the use of X-rays. Knowledge, i.e., as to the position of defects in the tire sidewall, permits the reduction of X-ray images to a small circumference area of the tire, i.e., in the region of the found defect. Thus, X-raying of the entire circumference is not required. Consequently, it is also possible to use simpler X-ray devices which may only test sections of a tire.

Another feature of the present invention provides for a preferable rotation mechanism that may be simply embodied with a small number of structural components. If the pneumatic vehicle tire under test remains in frictional contact with a friction device, e.g., due to its own weight, the production and maintenance of the drive contact may be ensured in a simple manner. Further, the present invention may provide a support for the tire in which the tire to be tested may be inserted onto a laterally inclined plane and, thus, positioned in a laterally tilted support position. A lateral portion of the tire may rest on the lateral support faces and the tire may be inserted or removed from a different side.

In accordance with a further embodiment, the present invention may include a rotating friction device, which may remain in frictional contact with the tread after the tire has been inserted so that the inserted tire may be immediately rotatable. Due to the production and maintenance of the frictional contact, which may operate under its own weight atop the test piece, the operation of the device immediately after inserting the tire is reliably ensured. Parallel support rollers, which may be utilized for supporting the tread, may have radially extending shoulders formed thereon to cooperate with a support face of an additional support roller having a radial direction component. The support face of the additional support roller may be coplanar with the lateral support face of the extending shoulders with each of the support faces cooperating with a lateral side of the inclined tire under test. The support face may also be parallel to an equatorial plane of the tire test piece in the measurement position. Thus, the present invention may be utilized to form a laterally co-rotatable support face that ensures simple support of the tire under test with a reliable, low-loss ability to rotate.

The device may be particularly simple if one of the support rollers is the driven friction roller.

A further embodiment of the device in accordance with the features of the present invention may permit simple positioning of the sensor into a predetermined radial position in the region of the sidewall of a tire, i.e., independent of the overall dimensions of the tire. After insertion of the tire into the device, a securing device of the sensor for detecting defects may be radially moved toward the tread until a desired radial position for measuring is reached. The present invention may utilize a device for determining the radial position to assist in recognizing the desired radial position. After detecting the radial position, a securing device may be moved radially outward and the test piece may be removed from the device. In accordance with another embodiment, the distance between the sensor and tread of each tire blank or pneumatic vehicle tire inserted into the device may be determined when the tire is rotated in a radial direction. The distance may be independent of the tire dimension. Further, a predetermined spacing of the sensor to the tread may also be automatically set, and, consequently, a radial position of the sensor corresponding to the predetermined spacing may be automatically set for detection in the radial sidewall region. In a structurally simple manner that can also be reliably automated without additional control expenditure, the sensor, for the purpose of distance averaging, may include a follower roll coupled to a proximity switch, so that upon contact with the tread, the follower roll automatically actuates a proximity switch and stops the radial movement of the sensor.

In accordance with still another feature of the present invention, the device may include a rolling stand, a guide rail, and a securing device that may form a sled for radial movement. Further, a device for moving the sled in the track, e.g., a ball bearing-supported spindle, may be utilized. Thus, this embodiment provides radial shifting movement and permits a very precise adjustment and maintenance of the radial position.

A further embodiment of the present invention permits a particularly simple and individually automated adjustment of an optimized lateral spacing between the sidewall and the sensor for detecting arrangement and/or positioning defects of the reinforcement members. The optimized lateral spacing may be adjusted as a function of a measured value of the lateral spacing by the adjusting device. Thus, the measurement position of the sensor for detecting arrangement or position defects may be ensured, and may, to a large extent be uninfluenced by other disturbance variables and independent of tire dimension. Further, the measuring position of the sensor may be established without contacting the test piece. Another embodiment in accordance with the features of the present invention may represent a particularly simple, reliable manner for automatic lateral position adjustment of the sensor. In terms of its position, the sensor may be moved into the measurement position by a simple spindle drive mechanism.

It may be preferable for the device to include a sensor for detecting positioned on both sides of the space for receiving the tire blank or the pneumatic vehicle tire to be tested and to rotatably support it. In this manner, both sides of the tire under test may be simultaneously examined for defects. Through the use of one sensor, e.g., having a fixed lateral position relative to the sidewall of the rotatably supported pneumatic vehicle tire or tire blank to be tested, the spacing may be fixed, and, therefore, independent of the tire after it is inserted. After insertion, another laterally adjustable sensor for detection may be set at a predetermined spaced position relative to the opposite sidewall. Accordingly, independent of the thickness of the tire under test, the desired spacing between the fixed sensor and the associated tire sidewall may be consequently produced by insertion of the tire or the tire blank into the support mechanism. Without creating a hindrance during insertion, the second sensor for detection may be set into the desired spacing position of the other tire sidewall.

The present invention may be directed to a device for detecting defects in an arrangement of reinforcing members in casing plies in a sidewall region of at least one of an unvulcanized tire blank and a vulcanized pneumatic vehicle tire to be tested. The reinforcing members may include a magnetizable material and the device may include a support device that rotatably supports the at least one of the unvulcanized tire blank and the vulcanized pneumatic vehicle tire in rotation around a rotational axis and at least one sensor that detects magnetic field intensities in a heterogeneous magnetic field resulting from inductions generated by the defects in the arrangement of the reinforcing members moving through or in the heterogeneous magnetic field. The at least one sensor may be positioned in a radial measuring position in a radial region of the sidewall. The device may also include an adjusting device that adjusts a radial position of the at least one sensor into a radial set position of the tire in accordance with a diameter of the at least one of the unvulcanized tire blank and the vulcanized pneumatic vehicle tire, an adjusting device that adjusts an axial distance between the sensor and a sidewall of the at least one of the unvulcanized tire blank and the vulcanized pneumatic vehicle tire, a rotation controller that controls the rotation of the at least one of the unvulcanized tire blank and the vulcanized pneumatic vehicle tire, and an evaluation device coupled to the at least one sensor to receive the measured magnetic field intensities.

In accordance with another feature of the present invention, the rotation controller may include at least one rotationally driven, revolving friction member. The frictional contact between a tread of the at least one of the unvulcanized tire blank and/or the vulcanized pneumatic vehicle tire may occur at least during measurement of the magnetic field intensities.

In accordance with another feature of the present invention, the supporting device may include a support member to support the at least one of the unvulcanized tire blank and the vulcanized pneumatic vehicle tire in a position laterally inclined with respect to a vertical reference. The support member may include lateral support faces that rotatably support at least one of the unvulcanized tire blank and the vulcanized pneumatic vehicle tire in the laterally inclined position during measurement of the magnetic field intensities. The lateral support faces may include at least two parallel, rotatable rollers that support the tread and have shoulders for lateral support and at least one roller aligned parallel to an equatorial plane of the at least one of the unvulcanized tire blank and the vulcanized pneumatic vehicle tire in the laterally inclined position, and the at least one roller may provide lateral support.

In accordance with still another feature of the present invention, the device may also include a securing device for holding the at least one sensor. The securing device may be radially movable relative to the at least one of the unvulcanized tire blank and the vulcanized pneumatic vehicle tire as supported in the support device. The device may also include a detecting device that may detect a radial position of the moving sensor relative to the at least one of the unvulcanized tire blank and the vulcanized pneumatic vehicle tire as supported in the support device. The detecting device may be operatively coupled to the radial position adjusting device.

In accordance with a further feature of the present invention, the detecting device may include an additional sensor on the securing device. The additional sensor may be located radially outside the at least one of the unvulcanized tire blank and the vulcanized pneumatic vehicle tire and detecting device detects a distance between the additional sensor and the tread of the tire.

In accordance with a still further feature of the present invention, the device may include a rolling stand, a guide rail, and the securing device may include a sled for radial movement. The device may also include a sled moving device that moves the sled in a track and comprises a ball bearing-supported spindle.

In accordance with another feature of the present invention, the device may also include a detecting device for detecting a lateral distance between the sensor and the sidewall. The detecting device may be operatively coupled to the axial adjusting device.

In accordance with still another feature of the present invention, the at least one sensor may be supported for lateral movement and is operatively coupled to a controllably driven spindle that adjusts the lateral position of the at least one sensor.

In accordance with a still further feature of the present invention, the evaluation device may include a computer. The computer may determine average values of magnetic field intensities detected by the at least one sensor when the at least one of the unvulcanized tire blank and the vulcanized pneumatic vehicle tire is rotated over a first predetermined rotation angle range, and amplitude values of magnetic field intensity detected by the at least one sensor in a second rotation angle range. The computer may also compare each amplitude value of the second measurement with set values for a maximal permissible amplitude value. The device may also include an indicator device. The indicator device may indicate an angular position on the at least one of the unvulcanized tire blank and the vulcanized pneumatic vehicle tire of amplitudes that have been determined to be outside the maximal permissible amplitude value.

In accordance with another feature of the present invention, the device may also include at least one sensor located on both sides of support device. One of the sensors may be located in a lateral fixed position relative to a facing sidewall of the at least one of the unvulcanized tire blank and the vulcanized pneumatic vehicle tire and another of the sensors may be located for lateral adjustment.

In accordance with yet another feature of the present invention, the magnetizable material may include steel.

The present invention may be directed to a process for detecting defects in an arrangement of reinforcing members, made of a magnetizable material, in casing plies in a sidewall region of at least one of an unvulcanized tire blank or a vulcanized pneumatic vehicle tire. The process may include moving the reinforcing members in at least one of the unvulcanized tire blank and the vulcanized pneumatic vehicle tire, relative to a sensor, through a first angular range. The reinforcing members may be arranged to form an angle greater than 0° relative to a direction of movement. The process may also include measuring magnetic field intensities in a heterogeneous magnetic field resulting from inductions generated by the relative movement of the reinforcing members and the sensor, and averaging the measured magnetic field intensities to determine an average value. The process may also include moving the reinforcing member in the at least one of the unvulcanized tire blank and the vulcanized pneumatic vehicle tire, relative to the sensor, through a second angular range, and measuring the magnetic field intensities in the second angular range. The process may next include comparing the magnetic field intensities measured in the second angular range with the determined average value to determined deviation values, and comparing the deviation values with a set value that establishes a permissible limit. The process also includes indicating one of a rotational angle and a circumferential position on the at least one of the unvulcanized tire blank and the vulcanized pneumatic vehicle tire of locations where the deviation values exceed the set value. The indicated location may be indicative of the one of the rotational angle and the circumferential position of defects in the arrangement of adjacent reinforcing members.

In accordance with yet another feature of the present invention, after detecting the position of the arrangement defects of the adjacent reinforcing members, a size of the detected arrangement defects may be determined in an X-ray measurement process.

The present invention may be directed to a process for detecting defects in an arrangement of reinforcing members in casing plies in a sidewall region of at least one of an unvulcanized tire blank and a vulcanized pneumatic vehicle tire to be tested. The reinforcing members may include a magnetizable material, and the process may include rotatably supporting the at least one of the unvulcanized tire blank and the vulcanized pneumatic vehicle tire for rotation around a rotational axis, moving the reinforcing members past at least one sensor, and detecting, with the at least one sensor, magnetic field intensities in accordance with changes in a heterogeneous field due to the movement of the arrangement of reinforcing members past the at least one sensor. The process may also include adjusting a radial position of the at least one sensor into a radial set position of the tire in accordance with a diameter of the at least one of the unvulcanized tire blank and the vulcanized pneumatic vehicle tire, adjusting an axial distance between the sensor and a sidewall of the at least one of the unvulcanized tire blank and the vulcanized pneumatic vehicle tire, and rotatably controlling the rotation of the at least one of the unvulcanized tire blank and the vulcanized pneumatic vehicle tire. The process may also include receiving and evaluating the detected magnetic field intensities for defects in the arrangement of the reinforcing members.

In accordance with another feature of the present invention, the rotatably controlling step may include frictionally rotating the at least one of the unvulcanized tire blank and the vulcanized pneumatic vehicle tire with at least one rotationally driven, revolving friction member. Frictional contact between a tread of the at least one of the unvulcanized tire blank and the vulcanized pneumatic vehicle tire may occur at least during detection of the magnetic field intensity.

In accordance with another feature of the present invention, the rotatably supporting step may include supporting the at least one of the unvulcanized tire blank and the vulcanized pneumatic vehicle tire in a position laterally inclined with respect to a vertical reference, and supporting the at least one of the unvulcanized tire blank and the vulcanized pneumatic vehicle tire in the laterally inclined position during detection of the magnetic field intensity. At least two parallel, rotatable rollers may support the tread and have shoulders for lateral support and at least one roller may be aligned parallel to an equatorial plane of the at least one of the unvulcanized tire blank and the vulcanized pneumatic vehicle tire in the laterally inclined position. The at least one roller may provide lateral support.

In accordance with a further feature of the present invention, the process may also include holding the at least one sensor in a securing device. The securing device may be radially movable relative to the at least one of the unvulcanized tire blank and the vulcanized pneumatic vehicle tire as supported in the support device. The process may also include detecting a radial position of the moving sensor relative to the at least one of the unvulcanized tire blank and the vulcanized pneumatic vehicle tire as supported in the support device. The detecting device may be operatively coupled to the radial position adjusting device. Further, the process may include detecting a distance between the tire tread and an additional sensor. The additional sensor may be coupled to the securing device and may be located radially outside the at least one of the unvulcanized tire blank and the vulcanized pneumatic vehicle tire.

In accordance with still another feature of the present invention, the process may further include detecting a lateral distance between the sensor and the sidewall. The detected distance may be utilized for the adjusting of the axial distance between the sensor and the sidewall.

In accordance with a still further feature of the present invention, the measuring and evaluating step may include determining average values of magnetic field intensity detected by the at least one sensor when the at least one of the unvulcanized tire blank and the vulcanized pneumatic vehicle tire is rotated over a first predetermined rotation angle range, determining amplitude values of magnetic field intensity detected by the at least one sensor in a second rotation angle range, and comparing each amplitude value of the second measurement with set values for a maximal permissible amplitude value. The process may also include indicating an angular position on the at least one of the unvulcanized tire blank and the vulcanized pneumatic vehicle tire of amplitudes that have been determined to be outside the maximal permissible amplitude value.

In accordance with yet another feature of the present invention, the process may also include moving the reinforcing members in one of the unvulcanized tire blank and the vulcanized pneumatic vehicle tire, relative to a sensor, through a first angular range, wherein the reinforcing members are arranged to form an angle greater than 0° relative to a direction of movement, measuring resulting magnetic field intensities induced in a heterogeneous magnetic field by the relative movement, and averaging the measured resulting magnetic field intensity to determine an average value. The process may also include moving the reinforcing member in one of the unvulcanized tire blank and the vulcanized pneumatic vehicle tire, relative to the sensor, through a second angular range and measuring the resulting magnetic field intensities in the second angular range. The process may next include aligning the measured resulting magnetic field intensities in the second angular range with the average value, comparing the measured resulting magnetic field intensities in the second angular range with a set value that establishes a permissible limit, and indicating one of a rotational angle and a circumferential position on the at least one of the unvulcanized tire blank and the vulcanized pneumatic vehicle tire of locations where the measured resulting magnetic field intensities in the second angular range exceeds the set value. The indicated location may be indicative of the at least one of the rotational angle and the circumferential position of arrangement defects of adjacent reinforcing members.

The present invention may be directed to a device for detecting spacing defects between adjacent magnetizable reinforcing members located in casing plies in a sidewall region of test piece. The test piece may include at least one of an unvulcanized tire blank and a vulcanized pneumatic vehicle tire and the device may include at least one sensor that detects magnetic field intensities, a support device that rotatably supports the test piece in a direction of rotation, and a positioning device that positions the sensor adjacent the reinforcing members of the test piece. The at least one sensor may supply signals indicative of a spacing between adjacent reinforcing members. The device may also include an evaluation device for receiving the signals supplied from the at least one sensor to evaluate positions of spacing defects. The reinforcing members may be arranged for movement relative to the at least one sensor and arranged at an angle greater than 0° with respect to the direction of rotation of the test piece.

In accordance with another feature of the present invention, the at least one sensor may generate a heterogeneous magnetic field and detect changes in the heterogeneous magnetic field due to the movement of the reinforcing members.

In accordance with another feature of the present invention, the evaluation device may include a device for determining an average value for the detected magnetic field intensities.

In accordance with a further feature of the present invention, the evaluation device may further include a comparing device that compares the magnetic field intensities with the average value to find a deviation amount. The comparing device also compares the deviation amount with a permissible limit. When the deviation amount exceeds the permissible limit, a defect is identified and when the deviation amount does not exceed the permissible limit, no defect is identified.

In accordance with still another feature of the present invention, the positioning device may include an axial adjusting member for axially positioning the at least one sensor with respect to the test piece and a radial adjusting member for radially positioning the at least one sensor with respect to the test piece.

In accordance with a still further feature of the present invention, the device may further include a measurement head that carries the positioning device and the at least one sensor and may include a drive device for positioning the measurement head at a predetermined distance from a top portion of the test piece.

In accordance with yet another feature of the present invention, the measurement head may further include a proximity limit switch and a follower roller. When the follower roller contacts a top portion of the test piece, the proximity limit switch may be actuated to stop the drive device.

Other exemplary embodiments and advantages of the present invention may be ascertained by reviewing the present disclosure and the accompanying drawing.

BRIEF DESCRIPTION OF THE DRAWINGS

The present invention may be further described in the detailed description which follows, in reference to the noted plurality of drawings by way of non-limiting examples of preferred embodiments of the present invention, in which like reference numerals represent similar parts throughout the several views of the drawings, and wherein.

DETAILED DESCRIPTION OF THE PREFERRED EMBODIMENTS

The particulars shown herein are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for the fundamental understanding of the invention, the description taken with the drawing figure making apparent to those skilled in the art how the invention may be embodied in practice.

Figure 1A:
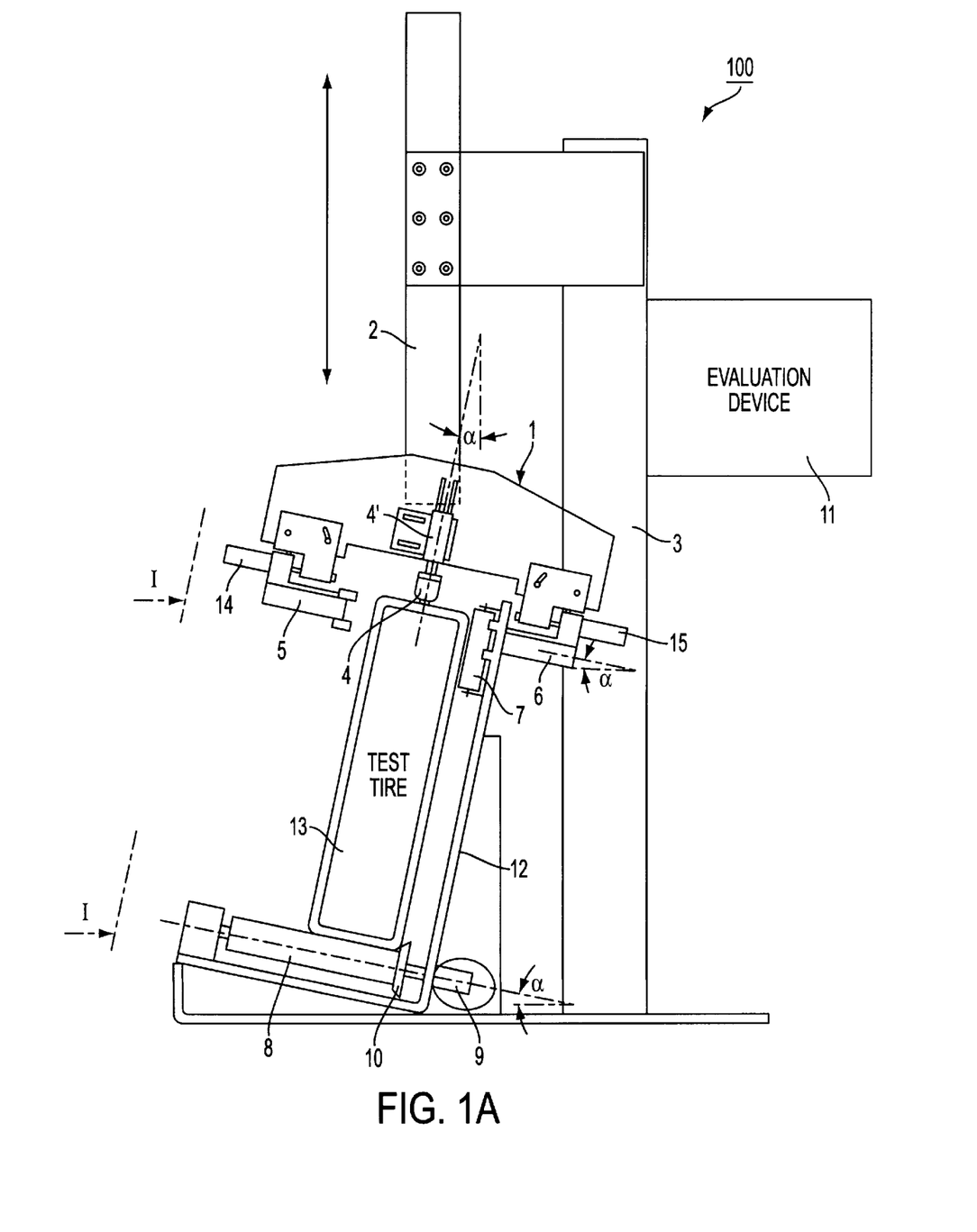
FIG. 1a illustrates a schematic representation of a testing device with a pneumatic vehicle tire inserted for testing.
Figure 1B:
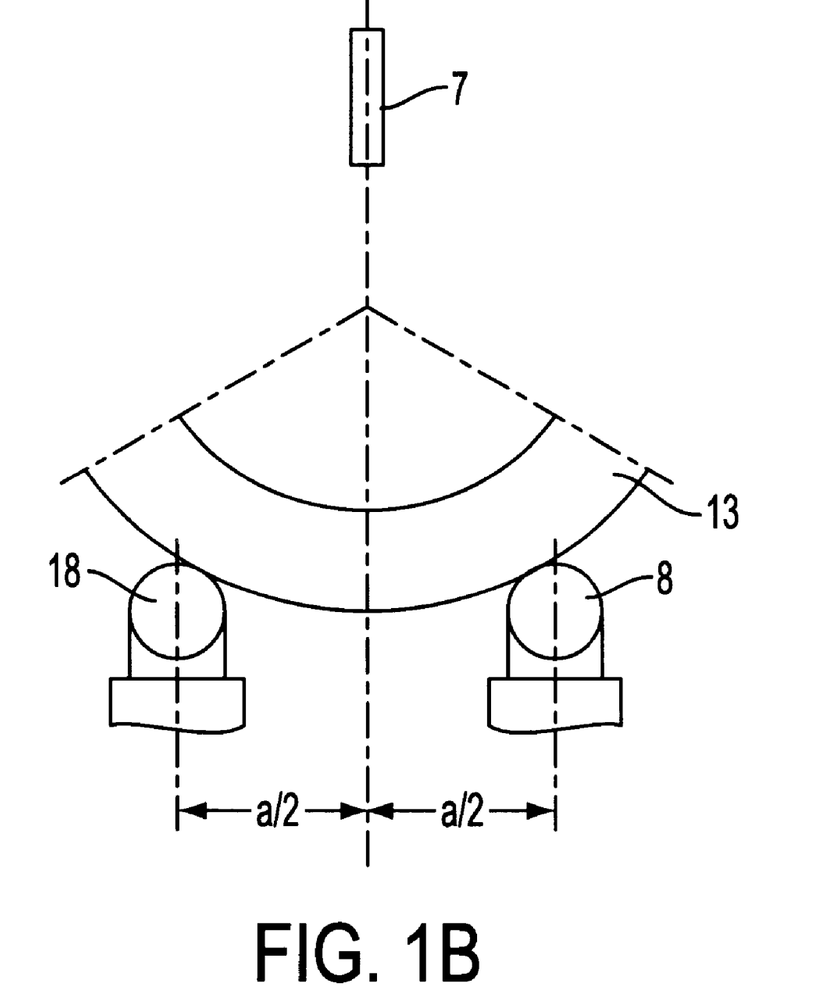
FIG. 1b illustrates a partial side view of the testing device with the pneumatic vehicle tire inserted for testing.

An exemplary testing device 100 for detecting arrangement or position defects in the spacing between reinforcing members in a pneumatic tire is illustrated in FIG. 1a. A vertical, downwardly directed guide rail 2 may be attached to a rolling stand 3 of testing device 100 and a measurement head 1 may be movably supported on guide rail 2. Utilizing a drive module of a known type, not shown, measurement head 1 may be raised or lowered in a controlled manner along guide rail 2 by a ball bearing-supported spindle mechanism (not shown). A support table 12 may be provided for receiving a tire to be tested. Support table 12 may include a lower part that retains a pair of parallel rollers, guide roller 18 and a drive roller 8. Guide roller 18 and drive roller 8, as shown in FIG. 1b, may be spaced from each other by a predetermined spacing a and each may each include a guide shoulder 10 with a support face facing the testing area for receiving the tire to be tested. Guide roller 18 and drive roller 8 may roll in a plane that encloses an angle α relative to a horizontal reference. Support table 12 may also include an upper region that rotatably supports a roller 7. A rotational axis of roller 7 may enclose an angle α, relative to a vertical reference, e.g., guide rail 2, and a tangent of roller 7, facing toward a testing area for receiving the tire to be tested, may be located in a common plane with the support face of guide shoulders 10. The common plane may enclose an angle α relative to the vertical reference. Roller 7 may also be located vertically above the plane formed by the axes of drive roller 8 and the guide roller 18.

To check for the existence of defects in the spacing of parallel reinforcing members, e.g., steel, in a casing sidewall region of a pneumatic vehicle tire or a toroid tire blank, a test piece 13 may be placed on drive roller 8 and support roller 18 so that a portion of the sidewall of the tire rests against each guide shoulder 10 of drive roller 8 and guide roller 18 and against roller 7. As illustrated in FIG. 1b, an extension of the rotational axis of roller 7 may vertically bisect a plane that includes the rotational axes of drive roller 8 and guide roller 18. Thus, the rotational axis of roller 7 may also bisect the predetermined spacing a between drive roller 8 and guide roller 18.

Figure 4:
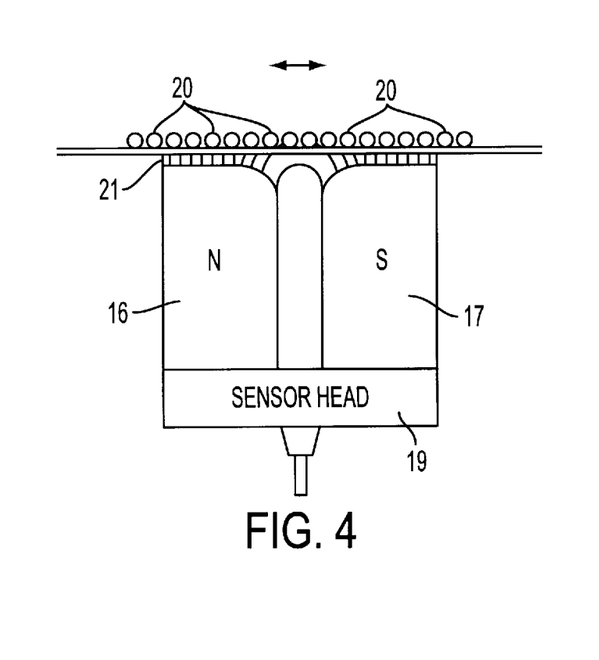
FIG. 4 illustrates a schematic representation of the positioning between a sensor and the shifting movement of the reinforcing members in the magnetic field leakage process of the present invention.

Sensors 5 and 6 may be coaxial with each other and coupled to downward extensions of measurement head 1. The coaxial positioning of sensors 5 and 6 may also enclose an angle a relative the vertical reference. Sensors 5 and 6 may be detectors for detecting magnetic field leakage. In particular, sensors 5 and 6 may be utilized to measure or detect magnetic field intensity in a heterogeneous magnetic field resulting from induction generated by movement of longitudinally oriented reinforcement members, e.g., steel cords, in their radial direction through the heterogeneous magnetic field. FIG. 4 shows an exemplary illustration of a sensor that may be utilized by the present invention. A sensor head 19 may include a north pole 16 and a south pole 17 of a permanent magnet that produces a heterogeneous magnetic field, indicated by field lines 21, outside the pole region. Parallel steel cords 20 may be oriented for testing so as to enclose an angle greater than 0° relative to an alignment of the north and south poles of the permanent magnet and may be moved in a direction indicated by the bidirectional arrow, i.e. with a directional component in the radial direction of the steel cords, first over one pole and then over the other pole. Sensor head 19 may detect changes of the heterogeneous magnetic field during the movement. Sensors 5 and 6 may, e.g., be a detector of the type SND 6 from the company Roland Electronik GmbH, D-7538 Keltern 2, which are generally usually for monitoring welding seams. Sensors 5 and/or 6 may also be coupled to an evaluation device 11 of a known type. A follower roller 4, coupled to a limit switch 4' may be located on measurement head 1 and positioned between sensors 5 and 6.

After test piece 13 has been inserted onto the device for testing, the tire tread may abut or contact a surface of guide roller 18 and a surface of drive roller 8, and, as discussed above, one of the sidewalls may be supported by shoulders 10 and roller 7. Thus, the tire under test may be placed in an inclined position that may be at an angle α relative to the vertical reference. Measurement head 1 may be moved by a drive mechanism, e.g., via a ball bearing-supported guide spindle, downward along guide rail 2 until follower roller 4 positioned on measurement head 1 comes into contact with the tread of test piece 13. The contact of follower roller 4 with the tread of test piece 13 may actuate proximity limit switch 4' and, therefore, stop the drive mechanism of the measurement head 1 and hold measurement head 1 in this position as a set position. The position of roller 4 may be adjustably coupled to proximity limit switch 4' so as to enable a selectable set position to ensure that sensors 5 and 6 are positioned at a radial position of the test piece 13, which includes the central sidewall region of the test piece. The positions of sensors 5 and 6 may be preset such that a predetermined spacing, e.g., approximately 2 mm, may be provided between the sensors and the respective facing sidewall of the tire under test. Further, sensor may be coaxially movable and adjustable relative to sensor 6 on measurement head 1. Still further, the present invention may additionally utilize a known distance sensor, e.g., a capacitive distance-measuring sensor, which may be coupled to sensor 5 to measure the distance to the facing sidewall of the test piece 13. The distance between sensor 5 and the facing sidewall may be determined, and sensor 5 may be moved by an adjusting motor 14 of a known type, e.g., a ball-bearing supported drive spindle, toward the facing sidewall until the predetermined spacing distance, e.g., approximately 2 mm, is determined. Because sensor 5 will be optimally positioned relative to the reinforcing members, adjusting motor 14 will stop the movement of sensor 5.

Once the sensors are properly positioned relative to the tire under test, drive roller 8 may be rotated by a controlled drive motor 9 of a known type. For example, due to frictional forces between the tread surface of the tire and the surface of drive roller 8, the rotation of drive roller 8 will correspondingly drive the tire under test 13 into rotation about its own axis. Further, according to the present invention, the weight of the test piece 13, i.e., downwardly supported against drive roller 8 and guide roller 18 and supported against shoulders 10 and roller 7, is sufficient to provide the necessary friction to rotate test piece 13 for testing.

Test piece 13 may be first rotated by approximately 90° so that sensors 5 and 6 may monitor the arrangement or position of reinforcement member 20. It is noted that the reinforcement members, e.g., steel cords, in the sidewall region are substantially parallelly aligned to form an angle of greater than 0° with respect to the direction of movement past sensors 5 and 6, i.e., the cords are not arranged parallel to the direction of movement. Spacing between adjacent reinforcing members induce a change of the heterogeneous magnetic field. Such that, any spacing between adjacent reinforcing members that is too large will be detected by sensors 5 and 6. Further, the signals from sensors 5 and 6 may be forwarded to an evaluation device 11, e.g., a computer, so that a graphical representation or plot of the resulting magnetic field intensity may be viewed by the technician.

The graphical plot of the resulting magnetic field intensity measured at the circumferential region over the first 90° may be averaged by evaluation device 11 to be used as a reference value for the further measurements. Test piece 13 may now be rotated 360° so that sensors 5 and 6 may measure the resulting magnetic field intensity through an entire rotational range of the tire and transmit the same to evaluation device 11. Evaluation device 11 may determine whether deviations of the resulting magnetic field intensity, e.g., with respect to the average or reference value occur during the 360° rotation, exceed a predetermined permissible tolerance. An exemplary graphical representation of a 360° rotation of test piece 13 is shown in FIG. 2.

Figure 2:
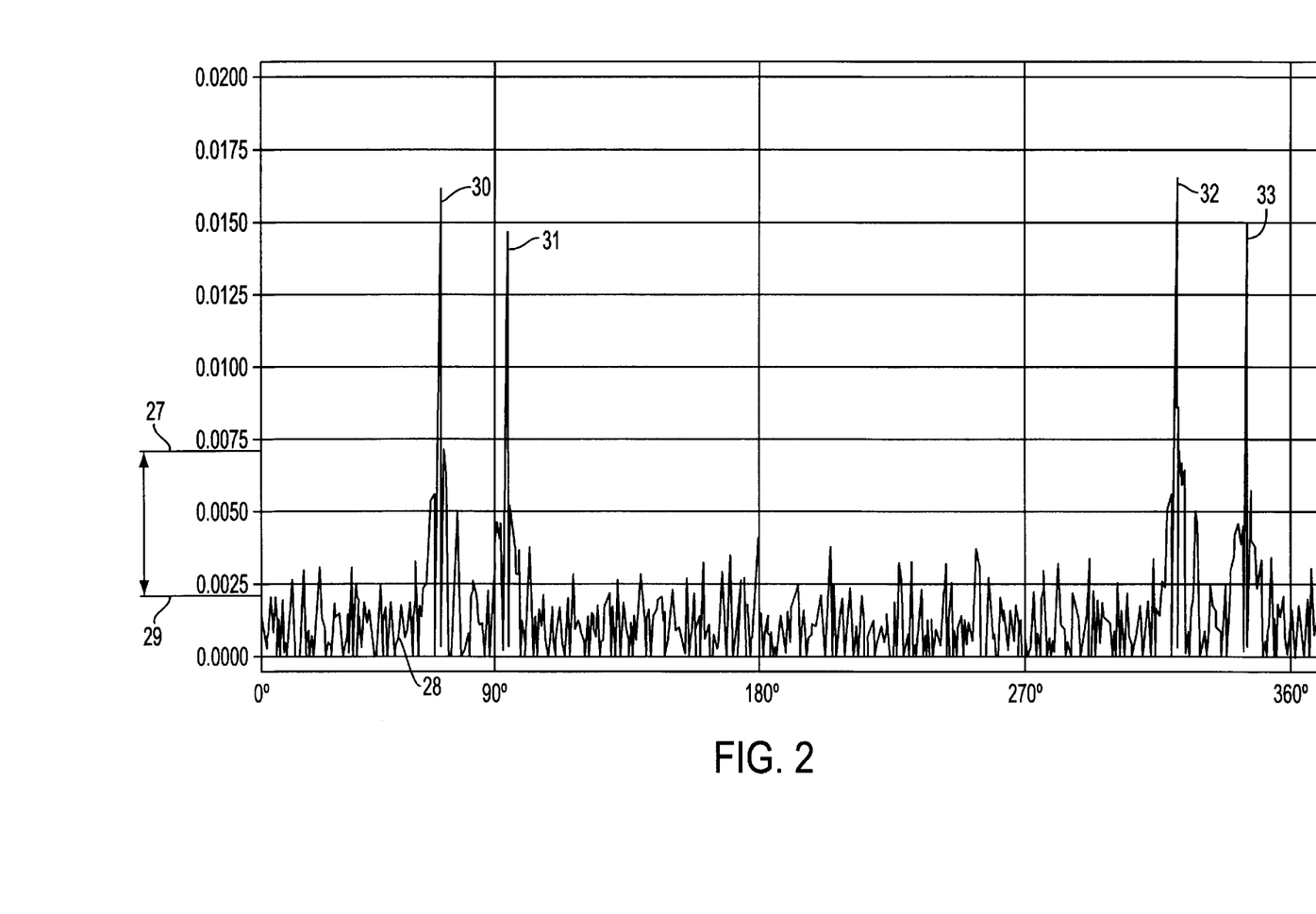
FIG. 2 illustrates a schematic diagram of a graphical plot of magnetic field intensity determined over the tire circumference of a tire to determine spacing defects in the arrangement or positioning between adjacent reinforcing members.

The abscissa of the graph of FIG. 2 represents a rotational angle α of test piece 13. The ordinate represents a scaled magnetic field intensity. Curve 28 represents the resulting magnetic field intensity measured by sensor 5 or 6. A limit value 27 may be set by the user as in indication of the maximum permissible resulting magnetic field intensities that may occur. An average value 29 represents the average value determined from the initial examination of the test piece 13, i.e., through the 90° rotation of test piece 13 discussed above. Limit value 27 may be set relative to average value 29 in accordance with a predetermined measurement variance $\Delta_{permiss}$, which represents a permissible spacing deviation from the desired spacing. The amplitudes of curve 28 that exceed limit value 27 indicate a position of defects, i.e., in which an excessively large spacing occurs between adjacent steel cords. In FIG. 2, these defects are indicated at positions 30, 31, 32, and 33. As noted above, the abscissa reveals the associated angular position of each defect on the test piece 13.

FIG. 2 provides an exemplary illustration of only the particularly dangerous deviations that lie above the average value and indicates the position of these defects resulting from excessively large cord spacings. If necessary or desired by the particular application of the present invention, an additional tolerance value may be utilized to indicate spacings that are too narrow. Thus, the present invention may also be utilized to plot this tolerance value, i.e., below the average value, and to locate the angular position of the excessively narrow spacing defect in a manner commensurate with the above-discussed manner of identifying and locating defects.

Test piece 13 may be rotated, e.g., in order from 0° to 360°, through the angular positions corresponding with defects 30, 31, 32, and 33 so that the location of each defect may be respectively and successively disposed opposite a marking device of a known type (not shown), e.g., a pointer coupled to rolling stand 3, for placing a predetermined mark on test piece 13 where the defect occurs. The position of the defect on test piece 13 may be indicated, e.g., manually or automatically, directly on test piece 13 by, e.g., color. It is likewise conceivable that, in lieu of the mechanical pointer, that position may be marked directly on the test piece with, e.g., a controlled marking pen of a known type. It is also conceivable that a marker of this kind may be included with sensor 5 or 6.

The distance between each of sensors 5 and 6 and the respective facing sidewall of the tire to be tested may be selected to prevent contact occurring between the sensors and the tire, but to enable the location of the sensors relative to the respective sidewall to be close enough so that the cords may be moved past the magnet in the sensor head to ensure reliable detection, e.g., approximately 2 mm.

After the measurement, adjusting motor 14 may move sensor 5 laterally away from test piece 13, and measurement head 1 may be raised along guide rail 2 via an appropriate driving device, e.g., the driven, ball bearing-supported spindle. Test piece 13 may be removed from drive roller 8 and guide roller 18, e.g., by rolling laterally downward. Motor 14, motor 9, and a drive module for lowering or raising measurement head 1 may be connected to computer 11 and may be controlled by it.

Second sensor 6 may be attached at a predetermined distance from a support plane of test piece 13, i.e., the sidewall surface. It is also conceivable that sensor 6 may be coaxially adjustable relative to sensor 5 and laterally adjustable relative to the sidewall, e.g., via an adjusting motor 15 which may include, e.g., a ball bearing-supported guide spindle. Fine tuning of the sensor spacing from the sidewalls, and subsequent adjustment during maintenance work, may be more easily accomplished by the adjustable sensors 5 and 6.

The present invention also contemplates providing input and storage for various tolerance set values for different test pieces. Accordingly, experimental value-based permissible tolerance for arrangement or positional deviations may be taken into account as a function of the production requirements of the respective tire under test.

If no deviations beyond the permissible tolerance value are found in test piece 13, test piece 13 may exit the testing device and be forwarded, e.g., down the production line. When deviations beyond the permissible tolerance value are detected, test piece 13 may be taken out of further production. It is also conceivable that, upon taking test piece 13 out of production, that defective test piece may be examined by the precision measurement of X-ray, e.g., in a known X-ray measuring device, to precisely determine the size and quality of defects. It is conceivable that, after X-ray examination, it may be determined that the defective tire may have some utility or particular potential uses. Otherwise, the defective test piece may be rejected and sorted out of the production line. Since the location of the arrangement or position defect is already known, e.g., marked, the X-ray measuring device may be utilized for testing only predefined sections of the defective tire.

Figure 3:
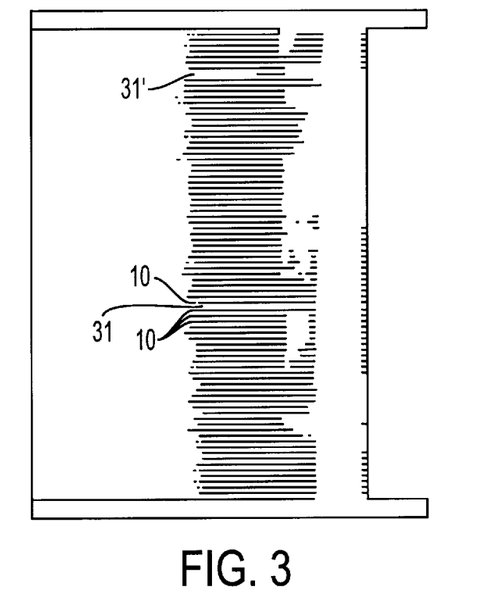
FIG. 3 illustrates an X-ray image for determining a size of the spacing in a region of the detected defect positions.

FIG. 3 illustrates a schematic X-ray image of a section of a defective tire, which may correspond to the vicinity around defect 31 shown in the graphical plot of FIG. 2. The X-ray image precisely indicates the varying sizes of spacings between adjacent reinforcing members in which each line indicates a reinforcing member 10. Thus, defects 31 and 31' are shown to have considerably enlarged spaces between adjacent steel cords 10 with respect to the other spacings.

If test piece 13 is a vulcanized pneumatic vehicle tire, once the pneumatic vehicle tire is found to be satisfactory, the tire may be directly supplied or forwarded either to other quality controls of a different type or may be finished for delivery.

If test piece 13 is a blank, once the blank is found to be satisfactory, the blank may be supplied or forwarded, e.g., to a vulcanizing device. If the blanks are found to have impermissible defects, the blanks may be reworked and again tested. Otherwise, the blanks are broken down into their individual component parts and may be reused. It is noted that after vulcanization, the blanks supplied to the vulcanizing process may be retested as finished pneumatic vehicle tires, as discussed in accordance with FIG. 1. As a result, defects in the spacings between adjacent steel cords in the sidewall region may also be detected that arose after the first measurement. These defects may occur during the swelling in the vulcanizing device and in the vulcanization. In this manner, non-reusable vulcanized tire waste may be reduced to the number of pneumatic vehicle tires that have only been encumbered with defects during this last manufacturing stage in the vulcanizing device.

A length of roller 7 may be selected to ensure a reliable support face for all conventional tire sizes.

Defects in the spacing between adjacent cords usually extend across the entire tire sidewall so that these defects may be reliably detected by sensors 5 and 6. In particular, in tires having very large sidewalls, for the purpose of increasing reliability, it is within the purview of the present invention to include at least one additional sensor for measuring the magnetic field leakage process. The additional sensor may be radially spaced apart from sensors 5 and 6 so that measurements may be simultaneously carried out at a number of radial positions.

It is noted that the foregoing examples have been provided merely for the purpose of explanation and are in no way to be construed as limiting of the present invention. While the invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the invention in its aspects. Although the invention has been described herein with reference to particular means, materials and embodiments, the invention is not intended to be limited to the particulars disclosed herein; rather, the invention extends to all functionally equivalent structures, methods and uses, such as are within the scope of the appended claims.

Reference Numeral List
1. measurement head
2. guide rail
3. rolling stand
4. roller
4'. proximity limit switch
5. detector
6. detector
7. roller
8. drive roller
9. drive motor
10. guide shoulder
11. evaluation device
12. support table
13. testpiece
14. adjusting motor
15. adjusting motor
16. north pole
17. south pole
18. guide roller
19. sensor head
20. reinforcing member; steel cord
21. heterogeneous magnetic field lines
27. limit value
28. tolerance
29. average value
30. defect
31. defect
32. defect
33. defect
100. testing device

What is claimed is:

1. A device for detecting defects in an arrangement of reinforcing members in casing, plies in a sidewall region of at least one of an unvulcanized tire blank and a vulcanized pneumatic vehicle tire to be tested, the reinforcing members comprising a magnetizable material, the device comprising:
 a support device capable of rotatably supporting the at least one of the unvulcanized tire blank and the vulcanized pneumatic vehicle tire for rotation around a rotational axis;
 at least one sensor capable of producing a heterogeneous magnetic field and measuring magnietic field intensities in the heterogeneous magnetic field resulting from inductions generated by defects in the arrangement of the reinforcing, members moving through the heterogeneous magnetic field;
 the at least one sensor is positioned in a radial measuring position in a radial region of the sidewall when the at least one of the unvulcanized tire blank and the vulcanized pneumatic vehicle tire is supported in the support device;
 a rotation controller capable of controlling rotation of the at least one of the unvulcanized tire blank and the vulcanized pneumatic vehicle tire; and
 an evaluation device coupled to the at least one sensor to receive the detected magnetic field intensities, the evaluation device comprising a threshold determining device capable of determining a threshold level from the measured magnetic field intensities, the threshold determining device being capable of calculating the threshold level from the measured magnetic field intensities, the threshold level corresponding to inductions indicating defects in the arrangement of the reinforcing members.

2. The device in accordance with claim 1, further comprising:
 an adjusting device capable of adjusting a radial position of the at least one sensor into a radial set position of the tire in accordance with a diameter of the at least one of the unvulcanized tire blank and the vulcanized pneumatic vehicle tire.

3. The device in accordance with claim 1, further comprising:
 an adjusting device capable of adjusting an axial distance between the at least one sensor and a sidewall of the at least one of the unvulcanized tire blank and the vulcanized pneumatic vehicle tire.

4. The device in accordance with claim 3, further comprising:
 an adjusting device capable of adjusting a radial position of the at least one sensor into a radial set position of the tire in accordance with a diameter of the at least one of the unvulcanized tire blank and the vulcanized pneumatic vehicle tire.

5. The device in accordance with claim 1, the rotation controller comprising at least one rotationally driven, revolving friction member,
 wherein frictional contact between a tread of the at least one of the unvulcanized tire blank and the vulcanized pneumatic vehicle tire occurs at least during detection of the magnetic field intensities.

6. The device in accordance with claim 1, the supporting device comprising a support member capable of supporting the at least one of the unvulcanized tire blank and the vulcanized pneumatic vehicle tire in a position laterally inclined with respect to a vertical reference, and the support member includes lateral support faces capable of rotatably supporting the at least one of the unvulcanized tire blank and the vulcanized pneumatic vehicle tire in the laterally inclined position during detection of the magnetic field intensities;
 wherein the lateral support faces include at least two parallel, rotatable rollers capable of supporting a tread of the at least one of the unvulcanized tire blank and the vulcanized pneumatic vehicle tire and include shoulders for lateral support of the at least one of the unvulcanized tire blank and the vulcanized pneumatic vehicle tire and wherein at least one roller is aligned parallel to an equatorial plane of the at least one of the unvulcanized tire blank and the vulcanized pneumatic vehicle tire in the laterally inclined position, and
 wherein the at least one roller is capable of providing lateral support to the at least one of the unvulcanized tire blank and the vulcanized pneumatic vehicle tire.

7. The device in accordance with claim 2, further comprising:
 a securing device for holding the at least one sensor, wherein the securing device is radially movable relative to the at least one of the unvulcanized tire blank and the vulcanized pneumatic vehicle tire as supported in the support device; and a detecting device capable of detecting a radial position of the at least one sensor relative to the at least one of the unvulcanized tire blank and the vulcanized pneumatic vehicle tire as supported in the support device;

wherein the detecting device is operatively coupled to the radial position adjusting device.

8. The device in accordance with claim 7, the detecting device comprising an additional sensor on the securing device, wherein the additional sensor is capable of being located radially outside the at least one of the unvulcanized tire blank and the vulcanized pneumatic vehicle tire and the detecting device is capable of detecting a distance between the additional sensor and a tread of the at least one of the unvulcanized tire blank and the vulcanized pneumatic vehicle tire.

9. The device in accordance with claim 7, further comprising:

a guide rail connected to the securing device;

a rolling stand connected to the guide rail;

the securing device comprising a sled for radial movement; and a sled moving device, for moving the sled in a track, comprising a ball bearing-supported spindle.

10. The device in accordance with claim 3, further comprising:

a detecting device capable of detecting a lateral distance between the at least one sensor and the sidewall, wherein the detecting device is operatively coupled to the axial adjusting device.

11. The device in accordance with claim 10, wherein the at least one sensor is supported for lateral movement and is operatively coupled to a controllably driven spindle that adjusts the lateral position of the at least one sensor.

12. The device in accordance with claim 1, the threshold determining device comprising a computer, wherein the computer is programmed to determine an average value of magnetic field intensities detected by the at least one sensor when the at least one of the unvulcanized tire blank and the vulcanized pneumatic vehicle tire is rotated over a first predetemined rotation angle range, wherein the computer is programmed to compare amplitude values of magnetic field intensities detected by the at least one sensor in a second rotation angle range, and wherein the computer compares each amplitude value of the second measurement with a set value for a maximal permissible amplitude value which set value corresponds to the average value of magnetic field intensity;

further comprising, an indicator device, wherein the indicator device is capable of indicating an angular position on the at least one of the unvulcanized tire blank and the vulcanized pneumatic vehicle tire of amplitudes that have been determined to be outside the maximal permissible amplitude value.

13. The device in accordance with claim 1, wherein the at least one sensor comprises at least one sensor located on each side of the support device, wherein the at least one sensor comprises a sensor located in a lateral fixed position relative to a facing sidewall of the at least one of the unvulcanized tire blank and the vulcanized pneumatic vehicle tire as supported and another sensor capable of lateral adjustment.

14. The device according to claim 1, the magnetizable material comprising steel.

15. A process for detecting defects in an arrangement of reinforcing members, made of a magnetizable material, in casing plies in a sidewall region of at least one of an unvulcanized tire blank and a vulcanized pneumatic vehicle tire, the process comprising:

moving the reinforcing members in the at least one of the unvulcanized tire blank and the vulcanized pneumatic vehicle tire, relative to a sensor that produces a heterogeneous magnetic field, through a first angular range, wherein the reinforcing members are arranged to form an angle greater than 0° relative to a direction of movement;

measuring magnetic field intensities in the heterogeneous magnetic field resulting from inductions generated by the relative movement of the rcinforcing members and the sensor;

averaging the detected magnetic field intensities of the first angular range to determine an average value;

moving the reinforcing members in the at least one of the unvulcanized tire blank and the vulcanized pneumatic vehicle tire, relative to the sensor, through a second angular range;

measuring the magnetic field intensities in the second angular range;

comparing, the magnetic field intensities measured in the second annular range with the average value to determine deviation values;

comparing the deviation values with a set value that establishes a permissible limit; and indicating one of a rotational angle and a circumferential position on the at least one of the unvulcanized tire blank and the vulcanized pneumatic vehicle tire of locations where the deviation values exceed the set value, wherein the indicated location is indicative of the at least one of the rotational angle and the circumferential position of detected defects in the arrangement of adjacent reinforcing members.

16. The process in accordance with claim 15, wherein, after detecting the position of the arrangement defects of the adjacent reinforcing members, a size of the detected arrangement defects is determined by X-ray measurement.

17. A process for detecting defects in an arrangement of reinforcing members in casing plies in a sidewall region of one of an unvulcanized tire blank and a vulcanized pneumatic vehicle tire to be tested, the reinforcing members comprising a magnetizable material, and the process comprising:

rotatably supporting the at least one of the unvulcanized tire blank and the vulcanized pneumatic vehicle tire for rotation around a rotational axis;

moving the reinforcing members past at least one sensor that produces a heterogeneous magnetic field;

measuring, with the at least one sensor, maonetic field intensities in the heterogeneous magnetic field resulting from inductions generated by defects in the arrangement of the reinforcing members moving past the at least one sensor;

rotatably controlling the rotation of the at least one of the unvulcanized tire blank and the vulcanized pneumatic vehicle tire;

determining an average value of magnetic field intensities measured by the at least one sensor when the at least one of the unvulcanized tire blank and the vulcanized pneumatic vehicle tire is rotated over a first predetermined rotation angle range;

determining amplitude values of magnetic field intensities measured by the at least one sensor in a second rotation angle range; and comparing each amplitude value of the second measurement with a set value of a maximal permissible amplitude value which set value corresponds to the average value of magnetic field intensities.

18. The process in accordance with claim 17, further comprising:
adjusting a radial position of the at least one sensor into a radial set position of the tire in accordance with a diameter of the at least one of the unvulcanized tire blank and the vulcanized pneumatic vehicle tire.

19. The process in accordance with claim 17, further comprising:
adjusting an axial distance between the at least one sensor and a sidewall of the at least one of the unvulcanized tire blank and the vulcanized pneumatic vehicle tire.

20. The process in accordance with claim 19, further comprising:
adjusting a radial position of the at least one sensor into a radial set position of the tire in accordance with a diameter of the at least one of the unvulcanized tire blank and the vulcanized pneumatic vehicle tire.

21. The process in accordance with claim 17, wherein rotatably controlling the rotation of the at least one of the unvulcanized tire blank and the vulcanized pneumatic vehicle tire comprises frictionally rotating the at least one of the unvulcanized tire blank and the vulcanized pneumatic vehicle tire with at least one rotationally driven, revolving friction member,
wherein frictional contact between a tread of the at least one of the unvulcanized tire blank and the vulcanized pneumatic vehicle tire occurs at least during measurement of the magnetic field intensities.

22. The process in accordance with claim 17, wherein rotatably controlling the rotation of the at least one of the unvulcanized tire blank and the vulcanized pneumatic vehicle tire comprises supporting the at least one of the unvulcanized tire blank and the vulcanized pneumatic vehicle tire in a position laterally inclined with respect to a vertical reference, and supporting the at least one of the unvulcanized tire blank and the vulcanized pneumatic vehicle tire in the laterally inclined position during measurement of the magnetic field intensities;
wherein at least two parallel, rotatable rollers support a tread of the at least one of the unvulcanized tire blank and the vulcanized pneumatic tire and have shoulders for lateral support of the at least one of the unvulcanized tire blank and the vulcanized pneumatic tire, and wherein at least one roller is aligned parallel to an equatorial plane of the at least one of the unvulcanized tire blank and the vulcanized pneumatic vehicle tire in the laterally inclined position, and
wherein the at least one roller provides lateral support to the at least one of the unvulcanized tire blank and the vulcanized pneumatic vehicle tire.

23. The process in accordance with claim 17, further comprising:
holding the at least one sensor in a securing device, wherein the securing device is radially movable relative to the at least one of the unvulcanized tire blank and the vulcanized pneumatic vehicle tire as supported in the support device; and
detecting with a detecting device a radial position of the at least one sensor relative to the at least one of the unvulcanized tire blank and the vulcanized pneumatic vehicle tire as supported in the support device;
wherein the detecting device is operatively coupled to the securing device.

24. The process in accordance with claim 23, further comprising detecting a distance between the tire tread and an additional sensor, wherein the additional sensor is coupled to the securing device, and is located radially outside the at least one of the unvulcanized tire blank and the vulcanized pneumatic vehicle tire.

25. The process in accordance with claim 17, further comprising:
detecting a lateral distance between the at least one sensor and the sidewall,
wherein the detected distance is utilized for adjusting an axial distance between the at least one sensor and the sidewall.

26. The process in accordance with claim 17, further comprising indicating an angular position on the at least one of the unvulcanized tire blank and the vulcanized pneumatic vehicle tire of amplitudes that have been detemlined to be outside the maximal permissible amplitude value.

27. The process in accordance with claim 17, wherein the reinforcing members are arranged to form an angle greater than 0° relative to a direction of movement of the at least one of the unvulcanized tire blank and the vulcanized pneumatic vehicle tire;
wherein comparing each amplitude value of the second measurement with the set value of the maximal permissible amplitude value comprises detemining deviation values by comparing the magnetic field intensities measured in the second angular range with the set value; and
further comprising indicating one of a rotational angle and a circumferential position on the at least one of the unvulcanized tire blank and the vulcanized pneumatic vehicle tire of locations where the deviation values exceed the set value,
wherein the indicated location is indicative of the at least one of the rotational angle and the circumferential position of detected defects in the arrangement of adjacent reinforcing members.

28. A device for detecting spacing defects between adjacent magnetizable reinforcing members located in casing plies in a sidewall region of a test piece comprising at least one of an unvulcanized tire blank and a vulcanized pnuematic vehicle tire, the device comprising:
at least one sensor capable of producing a magnetic field and detecting magnetic field intensities;
a support device capable of rotatably supporting the test piece in a direction of rotation;
a positioning device capable of positioning the at least one sensor adjacent the reinforcing members of the test piece;
the at least one sensor being capable of converting detected magnetic field intensities into a signal indicative of a spacing between adjacent reinforcing members;
an evaluation device capable of receiving the signal supplied from the at least one sensor to evaluate positions of spacing defects, the evaluation device comprising a threshold determining device capable of determining a threshold level from the measured magnetic field intensities, the threshold determining device being capable of calculating the threshold level from the measured magnetic field intensities, the threshold level corresponding to inductions indicating spacing defects between adjacent magnetizable reinforcing members; and the support device being capable of supporting the test piece such that the reinforcing members are arranged for movement relative to the at least one sensor and arranged at an angle greater than 0° with respect to the direction of rotation of the test piece.

29. The device in accordance with claim 28, the at least one sensor generating a heterogeneous magnetic field and detecting changes in the heterogeneous magnetic field due to the movement of the reinforcing members.

30. The device in accordance with claim 28, the evaluation device comprising a device capable of determining an average value of the detected magnetic field intensities.

31. The device in accordance with claim 30, the evaluation device further comprising a comparing device that compares the magnetic field intensities with the average value to find a deviation amount; and the comparing device further comparing the deviation amount with a permissible limit, wherein when the deviation amount exceeds the permissible limit, a defect is identified, and wherein when the deviation amount does not exceed the permissible limit, no defect is identified.

32. The device in accordance with claim 28, the positioning device comprising an axial adjusting member for axially positioning the at least one sensor with respect to the test piece and a radial adjusting member for radially positioning the at least one sensor with respect to the test piece.

33. The device in accordance with claim 28, further comprising a measurement head that carries the positioning device and the at least one sensor and comprises a drive device for positioning the measurement head at a predetermined distance from a top portion of the test piece.

34. The device in accordance with claim 33, the measurement head further comprising a proximity limit switch and a follower roller, wherein when the follower roller contacts a top portion of the test piece, the proximity limit switch is actuated to stop the drive device.

35. The device in accordance with claim 1, wherein the threshold determining device is capable of calculating the threshold level from an average magnitude of measured magnetic field intensities.

36. The process in accordance with claim 15, wherein comparing the magnetic field intensities and comparing the deviation values comprises determining the set value from a magnetude of the average value of the magnetic field intensities.

37. The process in accordance with claim 17, wherein comparing each amplitude value comprises determing the set value from a magnitude of the average value of the magnetic field intensities.

38. The device in accordance with claim 28, wherein the threshold determining device is capable of calculating the threshold level from an average magnitude of measured magnetic field intensities.

39. The device in accordance with claim 1, wherein a magnitude of the threshold level determined by the threshold determining device is dependent upon a magnitude of average magnetic field intensities.

40. The process in accordance with claim 15, wherein a magnitude of the set value is dependent upon a magnitude of the average value of magnetic field intensities.

41. The process in accordance with claim 17, wherein a magnitude of the set value is dependent upon a magnitude of the average value of magnetic field intensities.

42. The device in accordance with claim 28, wherein a magnitude of the threshold level determined by the threshold determining device is dependent upon a magnitude of average magnetic field intensities.

* * * * *